(12) United States Patent
Shimokawatoko et al.

(10) Patent No.: US 8,877,719 B2
(45) Date of Patent: Nov. 4, 2014

(54) PEST CONTROLLING COMPOSITION

(75) Inventors: Yasutaka Shimokawatoko, Kobe (JP); Emiko Sakamoto, Suita (JP); Mayuko Ozawa, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/388,303

(22) PCT Filed: Jul. 30, 2010

(86) PCT No.: PCT/JP2010/063339
§ 371 (c)(1),
(2), (4) Date: Feb. 1, 2012

(87) PCT Pub. No.: WO2011/018986
PCT Pub. Date: Feb. 17, 2011

(65) Prior Publication Data
US 2012/0129796 A1     May 24, 2012

(30) Foreign Application Priority Data
Aug. 11, 2009   (JP) ................. 2009-186379

(51) Int. Cl.
*A61K 31/70*       (2006.01)
*A01N 43/22*       (2006.01)

(52) U.S. Cl.
CPC ................... *A01N 43/22* (2013.01)
USPC ........................................ 514/28

(58) Field of Classification Search
USPC ..................................... 514/30, 28
See application file for complete search history.

(56) References Cited

U.S. PATENT DOCUMENTS

| | | | |
|---|---|---|---|
| 5,262,383 A | 11/1993 | Fischer et al. | |
| 6,114,374 A | 9/2000 | Lieb et al. | |
| 6,436,988 B1 | 8/2002 | Wachendorff-Neumann | |
| 7,754,749 B2 * | 7/2010 | Koradin et al. | 514/383 |
| 2003/0114312 A1 | 6/2003 | Fischer et al. | |
| 2008/0027114 A1 | 1/2008 | Funke et al. | |
| 2010/0130365 A1 | 5/2010 | Notten et al. | |
| 2010/0137233 A1 | 6/2010 | Fischer et al. | |
| 2010/0204167 A1 | 8/2010 | Fischer et al. | |
| 2010/0311677 A1 | 12/2010 | Fischer et al. | |
| 2011/0160054 A1 | 6/2011 | Breuningger et al. | |

FOREIGN PATENT DOCUMENTS

| | | |
|---|---|---|
| CA | 2428101 A1 | 5/2003 |
| DE | 19939395 A1 | 4/2000 |
| EP | 0528156 A1 | 2/1993 |
| EP | 2039248 A1 | 3/2009 |
| JP | 2000-516918 A | 12/2000 |
| JP | 2009-132670 A | 6/2009 |
| WO | 9700265 A1 | 1/1997 |
| WO | 0042850 A1 | 7/2000 |
| WO | 2008006513 A1 | 1/2008 |
| WO | 2008107097 A1 | 9/2008 |
| WO | 2009012909 A2 | 1/2009 |
| WO | 2009146793 A2 | 12/2009 |
| WO | 2010023171 A2 | 3/2010 |
| WO | 2010054757 A2 | 5/2010 |
| ZA | 9906662 A | 10/2000 |

OTHER PUBLICATIONS

Extended European Search Report issued Feb. 11, 2013 in EP Application No. 10808169.6.
Dripps et al, "Spinosad to spinetoram: Evolution of the spinosyns," The 236th ACS National Meeting, Philadelphia, PA, Aug. 17-21, 2008, retrieved from the Internet at http://oasys2.confex.com/acs/236nm/techprogram/P1208479 on Jan. 25, 2013.
Sparks et al, "Neural network-based QSAR and insecticide discovery: spinetoram," Journal of Computer-Aided MOlecular Design, vol. 22, No. 6-7, pp. 393-401 (Mar. 15, 2008).
Chloridis et al, "Spinetorarn (XDE-175): 1-7 a new spinosyn," Congress Proceedings / SVI International Plant Protection Congress, Glasgow, Scotland, Oct. 15, 2007, pp. 68-73.
Office Action issued Feb. 1, 2013 in CN Application No. 201080035337.6.
Int'l Search Report issued Sep. 7, 2010 in Int'l Application No. PCT/JP2010/063339.
Office Action issued Sep. 29, 2013 in CN Application No. 201080035337.6.

* cited by examiner

*Primary Examiner* — Elli Peselev
(74) *Attorney, Agent, or Firm* — Panitch Schwarze Belisario & Nadel LLP

(57) ABSTRACT

A pest controlling composition comprising spinetoram and a cyclic keto-enol compound having an acetyl CoA carboxylase-inhibiting activity as active ingredients.

2 Claims, No Drawings

PEST CONTROLLING COMPOSITION

TECHNICAL FIELD

The present invention relates to a pest controlling composition and a method of controlling a pest.

BACKGROUND ART

Spinetoram is known as an active ingredient of an insecticide (see, WO 97/00265).

Further, a cyclic keto-enol compound having an acetyl CoA carboxylase-inhibiting activity is known as an active ingredient of an insecticide (see, Japanese Patent Application National Publication (Laid-Open) No. 2000-516918, EP 528156A, and WO 00/42850)

DISCLOSURE OF THE INVENTION

These active ingredients of insecticides do not show a sufficient insecticidal effect in some cases. Thus, it is required to develop an insecticidal composition showing a more excellent insecticidal effect than a single active ingredient of an insecticide.

The present invention has an object of providing a pest controlling composition having an excellent controlling effect on a pest, and a method of controlling a pest.

In the present invention, a synergistic pest controlling effect is obtained by simultaneous use of spinetoram and a cyclic keto-enol compound having an acetyl CoA carboxylase-inhibiting activity.

That is, the present invention is as follows.

[1] A pest controlling composition comprising spinetoram and a cyclic keto-enol compound having an acetyl CoA carboxylase-inhibiting activity as active ingredients.

[2] The pest controlling composition according to [1], wherein the cyclic keto-enol compound having an acetyl CoA carboxylase-inhibiting activity is spirotetramat, spirodiclofen or spiromesifen.

[3] The pest controlling composition according to [1] or [2], wherein the weight ratio of spinetoram to the cyclic keto-enol compound having an acetyl CoA carboxylase-inhibiting activity is from 100:1 to 1:800.

[4] A method of controlling a pest, said method comprising a step of applying effective amounts of spinetoram and a cyclic keto-enol compound having an acetyl CoA carboxylase-inhibiting activity to a pest or a habitat of a pest.

[5] The pest controlling method according to [4], wherein the cyclic keto-enol compound having an acetyl CoA carboxylase-inhibiting activity is spirotetramat, spirodiclofen or spiromesifen.

[6] The pest controlling method according to [4] or [5], wherein the weight ratio of spinetoram to the cyclic keto-enol compound having an acetyl CoA carboxylase-inhibiting activity is from 100:1 to 1:800.

[7] Use of spinetoram and a cyclic keto-enol compound having an acetyl CoA carboxylase-inhibiting activity for pest control.

EFFECT OF THE INVENTION

The pest controlling composition of the present invention exerts an excellent pest controlling effect.

DETAIL DESCRIPTION OF THE INVENTION

Spinetoram is a mixture of spinetoram J ((2R,3aR,5aR,5bS,9S,13S,14R,16aS,16bR)-2-(6-deoxy-3-O-ethyl-2,4-di-O-methyl-α-L-mannopyranosyloxy)-13-[(2R,5S,6R)-5-(dimethylamino)tetrahydro-6-methylpyran-2-yloxy]-9-ethyl-2,3,3a,4,5,5a,5b,6,9,10,11,12,13,14,16a,16b-hexadecahydro-14-methyl-1H-as-indaceno[3,2-d]oxacyclododecine-7,15-dione) and spinetoram L ((2R,3aR,5aS,5bS,9S,13S,14R,16aS,16bS)-2-(6-deoxy-3-O-ethyl-2,4-di-O-methyl-α-L-mannopyranosyloxy)-13-[(2R,5S,6R)-5-(dimethylamino)tetrahydro-6-methylpyran-2-yloxy]-9-ethyl-2,3,3a,5a,5b,6,9,10,11,12,13,14,16a,16b-tetradecahydro-4,14-dimethyl-1H-as-indaceno[3,2-d]oxacyclododecine-7,15-dione). In spinetoram, the mixing proportion of spinetoram J to spinetoram L is 50:50 to 90:10 in terms of weight ratio, and usually 70:30 to 90:10. Spinetoram can be produced, for example, by a method described in WO 97/00265.

Examples of the cyclic keto-enol compound having an acetyl CoA carboxylase-inhibiting activity include spirotetramat (cis-4-(ethoxycarbonyloxy)-8-methoxy-3-(2,5-xylyl)-1-azaspiro[4,5]dec-3-en-2-one), spirodiclofen (3-(2,4-dichlorophenyl)-2-oxo-1-oxaspiro[4,5]dec-3-en-4-yl 2,2-dimethylbutyrate), and spiromesifen (2-oxo-3-(2,4,6-trimethylphenyl)-1-oxaspiro[4,4]nona-3-en-4-yl 3,3-dimethylbutanoate).

Spirotetramat can be produced, for example, by a method described in Japanese Patent Application National Publication (Laid-Open) No. 2000-516918. Spirodiclofen can be produced, for example, by a method described in European Patent Application Publication EP 528156. Spiromesifen can be produced, for example, by a method described in WO 00/42850.

In the pest controlling composition of the present invention, the weight ratio of spinetoram to a cyclic keto-enol compound having an acetyl CoA carboxylase-inhibiting activity is in the range of usually 100:1 to 1:800, preferably 20:1 to 1:200.

The pest controlling composition of the present invention may be a simple mixture of spinetoram and a cyclic keto-enol compound having an acetyl CoA carboxylase-inhibiting activity, however, in a usual case, spinetoram, a cyclic keto-enol compound having an acetyl CoA carboxylase-inhibiting activity and an inert carrier are mixed, and if necessary, a surfactant and other adjuvants for formulation are added, thereby preparing an oil solution, emulsifiable concentrate, flowable formulation, wettable powder, granular wettable powder, dust and granule.

The pest controlling composition of the present invention contains spinetoram and a cyclic keto-enol compound having an acetyl CoA carboxylase-inhibiting activity in a total amount of usually 0.01 to 90 wt %, preferably 0.1 to 80 wt %.

The inert carriers to be used in formulation include solid carriers, liquid carriers and gaseous carriers.

Examples of the solid carriers include fine-powdery or granular materials composed of minerals such as kaolin clay, attapulgite clay, bentonite, montmorillonite, acid white clay, pyrophyllite, talc, diatomaceous earth, calcite and the like; natural organic substances such as corn cob powder, walnut shell powder and the like; synthetic organic substances such as urea and urea formaldehyde resin; salts such as calcium carbonate and ammonium sulfate; synthetic inorganic substances such as synthetic hydrated silicon oxide.

Examples of the liquid carriers include aromatic hydrocarbons such as xylene, alkylbenzene, methylnaphthalene; alcohols such as 2-propanol, ethylene glycol, propylene glycol, ethylene glycol monoethyl ether; ketones such as acetone, cyclohexanone and isophorone; vegetable oils such as soybean oil and cotton seed oil; petroleum aliphatic hydrocarbons; esters; dimethyl sulfoxide; acetonitrile; and water.

Examples of the gaseous carries include fluorocarbons, butane gas, LPG (liquefied petroleum gas), dimethyl ether, and carbon dioxide gas.

Examples of the surfactants include anionic surfactants such as an alkyl sulfate, alkyl aryl sulfonate, dialkyl sulfosuccinate, polyoxyethylene alkyl aryl ether phosphate, lignin sulfonate, naphthalene sulfonate formaldehyde polycondensate, styrene-acrylic acid copolymer and sodium methyl oleyl taurate; nonionic surfactants such as a polyoxyethylene alkyl aryl ether, polyoxyethylene alkyl polyoxypropylene block copolymer and sorbitan fatty acid ester; and cationic surfactants such as an alkyl trimethyl ammonium salt.

Examples of the other adjuvants for formulation include water-soluble polymers such as polyvinyl alcohol, and polyvinyl pyrrolidone; polysaccharides such as gum Arabic, alginic acid and salts thereof, CMC (carboxymethylcellulose) and xanthan gum; inorganic substances such as aluminum magnesium silicate, smectite and alumina sol; antiseptic agents such as 5-chloro-2-methyl-4-isothiazolin-3-one, 1,2-benzothiazolin-3-one and 2-bromo-2-nitropropane-1,3-diol; coloring agents and, stabilizers such as PAP (acidic isopropyl phosphate), and BHT.

Examples of pests on which the pest controlling composition of the present invention exerts a controlling effect include arthropods such as insects, mites and the like, and nemathelminths such as nematodes. Specific examples of the pests include the following organisms.

Hemiptera harmful insects: Cicadellidae such as *Nephotettix cincticeps* and *Nephotettix virescens*; Aphidoidea such as *Aphis gossypii, Myzus persicae, Brevicoryne brassicae, Macrosiphum euphorbiae, Aulacorthum solani, Rhopalosiphum padi* and *Toxoptera citricidus*; stink bugs such as *Nezara antennata, Riptortus clavetus, Leptocorisa chinensis, Eysarcoris parvus, Halyomorpha mista* and *Lygus lineolaris*; whitefly such as *Trialeurodes vaporariorum, Bemisia tabaci, Bemisia argentifolii* and *Aleurocanthus spiniferus*; Coccoidea such as *Aonidiella aurantii, Comstockaspis perniciosa, Unaspis citri, Ceroplastes rubens, Icerya purchase* and *Pseudaulacapsis pentagona*; Tingidae, Psyllidae;

Lepidoptera harmful insects: Pyralidae such as *Chilo suppressalis, Tryporyza incertulas, Cnaphalocrocis medinalis, Notarcha derogata, Plodia interpunctella, Ostrinia furnacalis, Ostrinia nubilaris, Hellula undalis* and *Pediasia teterrellus*; Noctuidae such as *Spodoptera litura, Spodoptera exigua, Pseudaletia separata, Mamestra brassicae, Agrotis ipsilon, Plusia nigrisigna, Trichopulsia* spp., *Heliothis* spp., *Helicoverpa* spp.; Pieridae such as *Pieris rapae*; Tortricidae such as *Adoxophyes* spp., *Grapholita molesta, Leguminivora glycinivorella, Matsumuraeses azukivora, Adoxophyes orana fasciata, Adoxophyes* SP., *Homona magnanima, Archips fuscocupreanus* and *Cydia pomonella*, Gracillariidae such as *Caloptilia theivora* and *Phyllonorycter ringoneella*; Carposinidae such as *Carposina niponensis*; Lyonetiidae such as *Lyonetia* spp.; Lymantriidae such as *Lymantria* spp., *Euproctis* spp.; Yponomeutidae such as *Plutella xylostella* and the like; Gelechiidae such as *Pectinophora gossypiella, Phthorimaea operculella*; Arctiidae such as *Hyphantria cunea*; Tineidae such as *Tinea translucens, Tineola bisselliella*, etc.;

Thysanoptera harmful insects: Thysanoptera such as *Frankliniella occidentalis, Thrips parmi, Scirtothrips dorsalis, Thrips tabaci, Frankliniella intonsa, Frankliniella fusca*, etc.;

Diptera harmful insects: Agromyzidae such as *Musca domestica, Culex popiens pallens, Tabanus trigonus, Hylemya antiqua, Hylemya platura, Anopheles sinensis, Agromyza oryzae, Hydrellia griseola, Chlorops oryzae, Liriomyza trifolii; Dacus cucurbitae, Ceratitis capitata*;

Coleopterous harmful insects: *Epilachna vigintioctopunctata, Aulacophora femoralis, Phyllotreta striolata, Oulema oryzae, Echinocnemus squameus, Lissorhoptrus oryzophilus, Anthonomus grandis, Callosobruchus chinensis, Sphenophorus venatus, Popillia japonica, Anomala cuprea, Diabrotica* spp., *Leptinotarsa decemlineata, Agriotes* spp., *Lasioderma serricorne, Anthrenus verbasci, Tribolium castaneum, Lyctus brunneus, Anoplophora malasiaca, Tomicus piniperda*;

Orthopterous harmful insects: *Locusta migratoria, Gryllotalpa africana, Oxya yezoensis, Oxya japonica*;

Hymenopterous harmful insects: *Athalia rosae, Acromyrmex* spp., *Solenopsis* spp.;

Blattodea harmful insects: *Blattella germanica, Periplaneta fuliginosa, Periplaneta americana, Periplaneta brunnea, Blatta orientalis*;

Acarine harmful insects: Tetranychidae such as *Tetranychus urticae, Panonychus citri, Oligonicus* spp.; Eriophydae such as *Aculops pelekassi*; Tarsonemidae such as *Polyphagotarsonemus latus; Brevipalpus*, Tuckerellidae; Acaridae such as *Tyrophagus putrescentiae* and the like; Pyroglyphidae such as *Dermatophagoides farinae, Dermatophagoides ptenyssnus*; Cheyletidae such as *Cheyletus eruditus, Cheyletus malaccensis, Cheyletus moorei*, etc.;

Nematode: *Aphelenchoides besseyi, Nothotylenchus acris*.

The pest controlling method of the present invention has a step of applying effective amounts of spinetoram and the cyclic keto-enol compound having an acetyl CoA carboxylase-inhibiting activity to a pest or a habitat of a pest.

Examples of the habitat of a pest include crops and soils for growing crops.

The pest controlling method of the present invention can be carried out by applying a pest controlling agent of the present invention to a pest or a habitat of a pest. The pest controlling method of the present invention can also be carried out by applying spinetoram and a cyclic keto-enol compound having an acetyl CoA carboxylase-inhibiting activity, separately, to a pest or a habitat of a pest.

In the pest controlling method of the present invention, the weight ratio of spinetoram to a cyclic keto-enol compound having an acetyl CoA carboxylase-inhibiting activity is in the range of usually 100:1 to 1:800, preferably 20:1 to 1:200.

In the pest controlling method of the present invention, the method of applying spinetoram and a cyclic keto-enol compound having an acetyl CoA carboxylase-inhibiting activity to a habitat of a pest includes, for example, a method of spraying spinetoram and a cyclic keto-enol compound having an acetyl CoA carboxylase-inhibiting activity on stems and leaves of a crop, a method of irrigating a soil for growth of a crop with spinetoram and a cyclic keto-enol compound having an acetyl CoA carboxylase-inhibiting activity, and a method of treating seeds of a crop with spinetoram and a cyclic keto-enol compound having an acetyl CoA carboxylase-inhibiting activity.

In the case of treating stems and leaves of a crop or treating a soil for growth of a crop with spinetoram and a cyclic keto-enol compound having an acetyl CoA carboxylase-inhibiting activity, the treatment amount thereof can be varied depending on the kind of a crop as a control subject, the kind of a pest as a control subject, the degree of generation of a pest as a control subject, the formulation form, the treatment period, the weather condition and the like, and the total amount of spinetoram and a cyclic keto-enol compound having an acetyl CoA carboxylase-inhibiting activity is usually 0.1 to 1000 g, preferably 1 to 200 g per 10000 $m^2$.

When the active ingredients are prepared into an emulsifiable concentrate, wettable powder, flowable formulation and the like, these formulations are usually diluted with water and sprayed for treatment. In this case, the concentration of the active ingredients is diluted to usually 1 to 10000 ppm, preferably 10 to 500 ppm. When the active ingredients are prepared into a dust, granule and the like, these formulations are usually used as they are for treatment without dilution.

In the case of treatment of seeds of a crop with spinetoram and a cyclic keto-enol compound having an acetyl CoA carboxylase-inhibiting activity, the treatment amount thereof is usually 0.001 to 20 g, preferably 0.01 to 10 g in terms of the total amount of spinetoram and a cyclic keto-enol compound having an acetyl CoA carboxylase-inhibiting activity per kg of seeds.

The pest controlling composition of the present invention can be used for pest control of the following "crops" and the like.

"Crops"

Agricultural crops; corn, wheat, barley, rye, oat, sorghum, cotton, soybean, peanut, buckwheat, beet, rapeseed, sunflower, sugarcane, tobacco, and the like Vegetables; solanaceous vegetables (eggplant, tomato, green pepper, red pepper, potato), cucurbitaceous vegetables (cucumber, pumpkin, zucchini, watermelon, melon), brassicaceous vegetables (radish, turnip, horseradish, kohlrabi, napa cabbage, cabbage, mustard green, broccoli, cauliflower), asteraceous vegetables (cocklebur, crown daisy, artichoke, lettuce), liliaceous vegetables (Welsh onion, onion, garlic, asparagus and the like), umbelliferous vegetables (carrot, parsley, celery, parsnip), chenopodiaceous vegetables (spinach, chard), labiatae vegetables (Japanese basil, mint, basil), strawberry, sweet potato, Japanese yam, aroid and the like.

Flowering ornamental plants: *acanthus*, morning glory, *azalea, hydrangea, anemone raddeana, rhodohypoxis baurii, anemone, polygonatum odoratum, amaryllis, iris, alyssum, armeria, arctotis*, China aster, edible flower, *Bauera rubioides*, Cuban lily, *Hosta montana*, Mexican aster, four o'clock, *Hypericum*, oriental poppy, *gentiana makinoi, Hosta aureomarginata*, Japanese *iris, clematis patens, gazania*, Casa Blanca, carnation, showy lily, *gerbera, kalanchoe, calceolaria*, curry plant, Carolina jasmine, *canna, chrysanthemum, Brugmansia*, yellow *cosmos*, plantain lily, Kimjongilia, tea tree (Manuka), pot marigold, myrtle, *nasturtium, gladiolus*, Siam tulip, *clematis*, cockscomb, shrimp plant, midday flower, *cosmos, Hosta sieboldii, Convolvulus arvensis, Hosta sagae*, primrose, saffron *crocus, salvia, cyclamen*, moss *phlox, Paeonia lactiflora, Anemone hupehensis, Bletilla striata*, sweet pea, lily of the valley, snowflake, *portulaca*, violet, rose of Sharon, yarrow, Chinese pink, *zephyranthes, pelargonium, geum*, zepher lily, *dahlia, tithonia*, tulip, chocolate *cosmos, Vinca major, scilla*, downy myrtle, German *iris*, passionflower, *dianthus*, rape blossom, Madagascar periwinkle, soft windflower, *nemophila, Nerine*, swamp *chrysanthemum* (North pole), Japanese water *iris (iris ensata* var. *spontanea), verbena, hibiscus*, Joseph's coat, coral flower, Japanese water *iris (Iris ensata)*, eastern redbud, spring starflower, wavyleaf sea-lavender, California poppy, pansy, Virginia stock, daisy, corn poppy, Himalayan creeping saxifrage, sunflower, hyacinth, crape-myrtle, *Geranium, fuchsia, freesia, primula*, garden balsam, ground-cherry, peony, *Tricyrtis*, marguerite, marigold, *Gymnaster savatieri*, strawflower, *muscari*, Japanese *kerria*, lily, *ranunculus, lantana*, gentian, *Lupinus, lobelia*, and the like.

Ornamental foliage plants: ivy, cattail, *aglaonema, adiantum, asparagus, asplenium, ananas, aphelandra, alocasia, anthurium*, Indian rubber tree, *nepenthes, aechmea, aeschynanthus, episcia, strelitzia augusta*, spider plant, Chinese banyan, kapok, *caladium, calathea*, velvet plant (*Gynura*), *Guzumania, Ctenanthe*, gum tree, *crassula, croton, Alocasia odora*, orange jessamine, coffee tree, massangeana, conifers, *coleus, cordyline, columnea, sansevieria, sansevieria*, Chinese *ixora, schefflera, cissus, cyperus*, reed *rhapis*, silk jessamine, *syngonium, strelitzia, spathiphyllum, senecio, zebrina*, Japanese sago palm, *tillandsia, tupidanthus*, coral tree, *dizygotheca, dieffenbachia, duranta*, bottle palm, *dracaena, tradescantia, neoregelia, nephrolepis*, hearts vine, *hibiscus, pachypodium*, Guiana chestnut (*Pachira*), ponytail, staghorn fern, *pilea, fatshedera, ficus pumila, philodendron, bougainvillea, phoenix, fittonia, pteris*, bridal veil, *vriesea, plectranthus, begonia, peperomia, heliconia*, benjamina, poinsettia, *pothos, hoya, maranta*, Belgian evergreen, milkbush, oyster plant, *monstera*, palm, *yucca, lantana*, and the like;

Fruit trees; pomaceous fruits (apple, common pear, Japanese pear, Chinese quince, quince and the like), stony fruits (peach, plum, nectarine, Japanese plum, cherry, apricot, prune and the like), citruses (*Satsuma mandarin*, orange, lemon, lime, grape fruit and the like), nuts (chestnut, walnut, hazel, almond, pistachio, cashew nut, *macadamia* nut and the like), berry fruits (blue berry, cranberry, blackberry, raspberry and the like), grape, persimmon, olive, loquat, banana, coffee, date, coconut and the like, Trees other than fruit trees; tea plant, mulberry tree, flowering trees and shrubs, street trees (Japanese Ash, birch, dogwood, *eucalyptus*, ginkgo, lilac, maple, oak, poplar, *cercis*, Formosan sweetgum, *platanus, zelkova*, Japanese arborvitae, Japanese fir, hemlock fir, juniper, pine, spruce, yew) and the like.

The above-described "crops" include also plants having resistance to a herbicide such as a 4-Hydroxyphenylpyruvate dioxygenase inhibitor such as isoxaflutole and the like, an acetolactate synthase (hereinafter, abbreviated as ALS) inhibitor such as imazethapyr, thifensulfuron-methyl, a 5-enol-pyruvyl-shikimate-3-phosphate (hereinafter, abbreviated as EPSP) synthase inhibitor such as glyphosate, a glutamine synthase inhibitor such as glufosinate, an auxin type herbicide such as 2,4-D, dicamba, bromoxynil, which resistance has been imparted by a classical breeding method or a gene recombination technology.

Examples of the crop having the resistance imparted by a classical breeding method include a corn or canola which is resistant to imidazolinone ALS-inhibiting herbicides such as imazethapyr, and are already marketed under the trade name of Clearfield (registered trademark). There are STS soybean resistant to sulfonylurea ALS-inhibiting herbicides such as thifensulfuron methyl. Likewise, examples of the plants having resistance to acetyl CoA carboxylase inhibitors such as trione oximes, aryloxyphenoxypropionic acid herbicides imparted by a classical breeding method include SR cor. The plants endowed with resistance to acetyl CoA carboxylase inhibitors are described in Proc. Natl. Acad. Sci. USA (1990) vol. 87, pp. 7175 to 7179 and the like.

Examples of the "crop" having resistance to herbicides imparted by a gene recombination technology include corn, soybean and cotton resistant to glyphosate and glufosinate, and are already marketed under the trade name of RoundupReady (registered trademark), LibertyLink (registered trademark) and Optimum GAT (registered trademark) and the like.

Mutated acetyl CoA carboxylases which are resistant to acetyl CoA carboxylase inhibitors are reported in Weed Science (2005) vol. 53, pp. 728 to 746 and the like, and plants which are resistant to acetyl CoA carboxylase inhibitors can be produced by introducing such a mutated acetyl CoA carboxylase gene into a plant by a gene recombination technology or introducing a mutation correlated with resistance impartation into a plant acetyl CoA carboxylase. Further, plants which are resistant to acetyl CoA carboxylase inhibitors and ALS inhibitors and the like can be produced by introducing a base substitution mutation-introduced nucleic acid typified by chimera plasty technology (Gura T. 1999. Repairing The Genome's Spelling Mistakes. Science 285: 316-318) into a plant cell thereby introducing a site-specific amino acid substitution mutation into the acetyl CoA carboxylase gene and ALS gene and the like of the plant.

Crops such as soybean and the like which are resistant to dicamba can be produced by introducing a degrading enzyme for dicamba such as dicamba monooxygenase and the like isolated by Pseudomonas maltophilia into plants (Behrens et al. 2007 Dicamba Resistance: Enlarging and Preserving Biotechnology-Based Weed Management Strategies. Science 316: 1185~1188).

By introducing a gene coding aryloxyalkanoate dioxygenase, crops which are resistant to phenoxy acid herbicides such as 2,4-D, MCPA, dichloprop, mecoprop and the like and to aryloxyphenoxypropionate herbicides such as quizalofop, haloxyfop, fluazifop, diclofop, fenoxaprop, metamifop, cyhalofop, clodinafop and the like can be produced (WO2005/107437, WO2007/053482, WO2008/141154).

The above-described "crops" include also crops endowed with a capability of synthesizing an insecticidal protein known, for example, as genus Bacillus, by using a gene recombination technology.

Toxins expressed in such gene recombinant plants include insecticidal proteins derived from *Bacillus cereus* and *Bacillus popilliae*; δ-endotoxins such as Cry1Ab, Cry1Ac, Cry1F, Cry1Fa2, Cry2Ab, Cry3A, Cry3Bb1, Cry9C or the like derived from Bacillus thuringiensis; insecticidal proteins such as VIP1, VIP2, VIP3, VIP3A; nematode-derived insecticidal proteins; toxins produced by animals such as scorpion toxin, spider toxin, bee toxin, insect-specific neurotoxins; filamentous fungi toxins; plant lectin; agglutinin; protease inhibitors such as trypsin inhibitor, serine protease inhibitor, patatin, cystatin, papain inhibitor; ribosome inactivation proteins (RIP) such as lysine, corn-RIP, abrin, luffin, saporin, briodin; steroid metabolizing enzymes such as 3-hydroxy steroid oxidase, ecdysteroid-UDP-glucosyltransferase, cholesterol oxidase; ecdysone inhibitors; HMG-CoA reductases; ion channel inhibitors such as a sodium channel inhibitor, calcium channel inhibitor; juvenile hormone esterase; diuretic hormone receptor; stilbene synthase; bibenzyl synthase; chitinase; glucanase.

Toxins expressed in such gene recombinant crops include also hybrid toxins, partially deficient toxins and modified toxins of δ-endotoxin proteins such as Cry1Ab, Cry1Ac, Cry1F, Cry1Fa2, Cry2Ab, Cry3A, Cry3Bb1, Cry9C, Cry34Ab, Cry35Ab or the like; and insecticidal proteins such as VIP1, VIP2, VIP3, VIP3A or the like. Hybrid toxins are produced by a new combination of different domains of these proteins using a recombination technology. As the partially deficient toxin, Cry1Ab in which a part of an amino acid sequence is deficient is known. In the modified toxin, one or more of amino acids in a natural-type toxin are substituted. Examples of these toxins and, recombinant plants capable of synthesizing these toxins are described in EP-A-0374 753, WO 93/07278, WO 95/34656, EP-A-0 427 529, EP-A-451 878, WO 03/052073 and the like. Toxins contained in these recombinant plants provide a plant with resistance, particularly, to coleopterous harmful insects, dipterous harmful insects and lepidopterous harmful insects.

Gene recombinant plants containing one or more insecticidal harmful insect-resistant genes and expressing one or more toxins are already known, and some of them are commercially marketed.

Examples of these gene recombinant plants include Yield Gard (registered trademark)(corn plant variety expressing Cry1Ab toxin), Yield Gard Rootworm (registered trademark) (corn plant variety expressing Cry3Bb1 toxin), Yield Gard Plus (registered trademark)(corn plant variety expressing Cry1Ab and Cry3Bb1 toxins), Herculex I (registered trademark)(corn plant variety expressing phosphinothricin N-acetyltransferase (PAT) for imparting resistance to Cry1Fa2 toxin and glufosinate), NuCOTN33B (registered trademark)(cotton plant variety expressing Cry1Ac toxin), Bollgard I (registered trademark)(cotton plant variety expressing Cry1Ac toxin), Bollgard II (registered trademark) (cotton plant variety expressing Cry1Ac and Cry2Ab toxins), VIPCOT (registered trademark) (cotton plant variety expressing VIP toxin), New Leaf (registered trademark) (potato plant variety expressing Cry3A toxin), Nature Gard (registered trademark), Agrisure (registered trademark), GT Advantage (GA21 glyphosate-resistant character), Agrisure (registered trademark) CB Advantage (Btll cone borer (CB) character), Protecta (registered trademark) and the like.

Examples of the plants to be used in the present invention include also plants endowed with resistance to Aphidoidea such as soybean containing an introduced Rag1 (Resistance Aphid Gene 1) gene, and the like.

The above-described "crops" include also crops endowed with a capability of producing an anti-pathogenic substance having a selective action, using a gene recombination technology.

As examples of the anti-pathogenic substance, PR proteins are known (PRPs, EP-A-0392 225). Such anti-pathogenic substances and gene recombinant plants producing them are described in EP-A-0 392 225, WO 95/33818, EP-A-0 353 191 and the like.

Examples of the anti-pathogenic substance to be expressed in such gene recombinant plants include ion channel inhibitors such as sodium channel inhibitors, calcium channel inhibitors (KP1, KP4, KP6 toxins and the like produced by virus are known); stilbene synthase; bibenzyl synthase; chitinase; glucanase; PR proteins; anti-pathogenic substances produced by microorganisms such as peptide antibiotics, antibiotics having a heterocyclic ring, protein factors correlated with plant disease resistance (referred to as plant disease resistant gene, and described in WO 03/000906).

The above-described crops include also plants endowed with useful characters such as an oil component modifying character, amino acid content enhancing character and the like, using a gene recombination technology. Examples thereof include VISTIVE (registered trademark) (low linolenic soybean having reduced linolenic acid content), high-lysine (high-oil) corn (corn having increased lysine or oil content).

Further, also included are stacked plant varieties obtained by combination of some of the above-described classical herbicide characters or herbicide-resistant genes, insecticidal harmful insect-resistant genes, anti-pathogenic substance producing genes, useful characters such as an oil component modifying character, amino acid content enhancing character.

In the present invention, pest controlling agents such as other kinds of insecticides, acaricides, nematocides, fungicides, herbicides, phytohormone agents, plant growth regulators; synergists, crop injury reducing agents, dyes, fertilizers, soil improving agents, animal feeding stuffs may be used together.

EXAMPLES

The present invention will be illustrated by formulation examples and test examples below, but the present invention is not limited to these examples.

First, formulation examples are shown. Parts are by weight.

Formulation Example 1

Five parts of spinetoram; 5 parts of spirotetramat, spiromesifen or spirodiclofen; 8 parts of polyoxyethylenestyryl phenyl ether; 2 parts of calcium dodecylbenzenesulfonate; and 80 parts of xylene are mixed to obtain an emulsifiable concentrate.

Formulation Example 2

Four parts of spinetoram; 20 parts of spirotetramat, spiromesifen or spirodiclofen; 3 parts of sodium dodecylbenzenesulfonate; 3 parts of sodium ligninsulfonate; and 70 parts of diatomaceous earth are pulverized by a jet air mill to obtain a wettable powder.

Formulation Example 3

Zero point five (0.5) parts of spinetoram; 1 part of spirotetramat, spiromesifen or spirodiclofen; 48.5 parts of talc; and 50 parts of clay are mixed to obtain a dust.

Formulation Example 4

One part of spinetoram; 4 parts of spirotetramat, spiromesifen or spirodiclofen; 5 parts of sodium dodecylbenzenesulfonate; 30 parts of bentonite; and 60 parts of clay are mixed. Then, a suitable amount of water is added to this mixture and the mixture is stirred, and this is granulated by a granulator and dried under air ventilation to obtain a granule.

Formulation Example 5

Five parts of polyoxyethylenestyryl phenyl ether sulfate; 20 parts of 1% xanthan gum aqueous solution; 3 parts of smectite mineral; and 60 parts of water are mixed. To this mixture is added 2 parts of spinetoram; and 10 parts of spirotetramat, spiromesifen or spirodiclofen, and the mixture is stirred, then, wet-pulverized by a sand mill to obtain a flowable formulation.

Formulation Example 6

Spinetoram (0.02 parts) and spirotetramat, spiromesifen or spirodiclofen (0.1 part) are dissolved in 10 parts of acetone. This solution is uniformly mixed with 99.88 parts of an animal solid feeding stuff powder (solid feeding stuff powder for breeding and reproduction CE-2: manufactured by CLEA Japan Inc.), then, acetone is air-dried to obtain a poison bait.

Formulation Example 7

Spinetoram (0.1 part) and spirotetramat, spiromesifen or spirodiclofen (0.1 part) are dissolved in 5 parts of xylene and 5 parts of trichloroethane, and this is mixed with 89.8 parts of deodorized kerosene to obtain an oil solution.

Next, test examples are shown for pest control according to the present invention.

Test Example 1

A flowable formulation containing 11.7 wt % of spinetoram (spinetoram J:spinetoram L=75:25 (weight ratio)) was diluted with water containing 0.02 vol % of a spreading agent (trade name: Sindain, manufactured by Sumitomo Chemical Co., Ltd.) so as to obtain a given concentration.

A flowable formulation containing 22.4 wt % of spirotetramat (trade name: Movento, manufactured by Bayer CropScience) was diluted with water containing 0.02 vol % of a spreading agent (trade name: Sindain, manufactured by Sumitomo Chemical Co., Ltd.) so as to obtain a given concentration.

The spinetoram water-diluted solution and spirotetramat water-diluted solution were mixed to prepare a test drug solution.

Cabbage was planted in a pot having a capacity of 860 ml and allowed to grow to 4-leaves stage. Leaves of the cabbage were cut one by one. One of the cabbage leaves was immersed in a test drug solution for 60 seconds. The cabbage leaf was air-dried, then, the cabbage leaf was placed in a cup having a capacity of 500 ml containing filter paper laid therein. Ten *Spodoptera litura* third-instar larvae were released in this cup. Four days after, life-or-death of the tested insects was observed. The results were corrected by the following formula, thereby calculating insecticidal ratio. The test was repeated three times. The results are shown in Table 1.

Insecticidal ratio (%)=100×($Mt$–$Mc$)/(100–$Mc$)

Mt: insect death ratio (%) in test compound-treated area

Mc: insect death ratio (%) in test compound-non-treated area

TABLE 1

| Active ingredient | Active ingredient concentration (ppm) | Insecticidal ratio (%) |
| --- | --- | --- |
| spinetoram + spirotetramat | 0.73 + 56 | 62.1 |
| spinetoram + spirotetramat | 0.73 + 112 | 72.4 |
| spinetoram | 0.73 | 17.2 |
| spirotetramat | 56 | 10.3 |
| | 112 | 20.7 |

Test Example 2

A flowable formulation containing 11.7 wt % of spinetoram (spinetoram J:spinetoram L=75:25 (weight ratio)) was diluted with water containing 0.02 vol % of a spreading agent (trade name: Sindain, manufactured by Sumitomo Chemical Co., Ltd.) so as to obtain a given concentration.

A flowable formulation containing 22.9 wt % of spiromesifen (trade name: CLEAZAR, manufactured by Bayer CropScience) was diluted with water containing 0.02 vol % of a spreading agent (trade name: Sindain, manufactured by Sumitomo Chemical Co., Ltd.) so as to obtain a given concentration.

The spinetoram water-diluted solution and spiromesifen water-diluted solution were mixed to prepare a test drug solution.

Cabbage was planted in a pot having a capacity of 860 ml and allowed to grow to 4-leaves stage. Leaves of the cabbage were cut one by one. One of the cabbage leaves was immersed in a test drug solution for 60 seconds. The cabbage leaf was air-dried, then, the cabbage leaf was placed in a cup having a capacity of 500 ml containing filter paper laid therein. Ten *Spodoptera litura* third-instar larvae were released in this cup. Four days after, life-or-death of the tested insects was observed. From the observed results, the insecticidal ratio was calculated in the same manner as in Test Example 1. The test was repeated three times. The results are shown in Table 2.

TABLE 2

| Active ingredient | Active ingredient concentration (ppm) | Insecticidal ratio (%) |
|---|---|---|
| spinetoram + spiromesifen | 0.73 + 112 | 41.4 |
| spinetoram | 0.73 | 6.9 |
| spiromesifen | 112 | 3.4 |

Test Example 3

A flowable formulation containing 11.7 wt % of spinetoram (spinetoram J:spinetoram L=75:25 (weight ratio)) was diluted with water containing 0.02 vol % of a spreading agent (trade name: Sindain, manufactured by Sumitomo Chemical Co., Ltd.) so as to obtain a given concentration.

A flowable formulation containing 22.4 wt % of spirotetramat (trade name: Movento, manufactured by Bayer CropScience) was diluted with water containing 0.02 vol % of a spreading agent (trade name: Sindain, manufactured by Sumitomo Chemical Co., Ltd.) so as to obtain a given concentration.

A flowable formulation containing 22.9 wt % of spiromesifen (trade name: CLEAZAR, manufactured by Bayer CropScience) was diluted with water containing 0.02 vol % of a spreading agent (trade name: Sindain, manufactured by Sumitomo Chemical Co., Ltd.) so as to obtain a given concentration.

These water-diluted solutions were mixed to prepare a test drug solution.

A kidney bean leaf piece having a diameter of about 2 cm was inoculated with 10 *Tetranychus urticae* female adult insects. Then, the test drug solution was sprayed in an amount of 0.3 ml per two pieces of the kidney bean leaves. Three days after, life-or-death of the female adult insects was observed. From the observed results, the insecticidal ratio was calculated in the same manner as in Test Example 1. The test was repeated three times.

The results are shown in Table 3.

TABLE 3

| Active ingredient | Active ingredient concentration (ppm) | Insecticidal ratio (%) |
|---|---|---|
| spinetoram + spirotetramat | 12.5 + 0.8 | 54.6 |
| spinetoram + spiromesifen | 12.5 + 3.2 | 82.1 |
| spinetoram | 12.5 | 28.4 |
| spirotetramat | 0.8 | 0 |
| spiromesifen | 3.2 | 28.0 |

INDUSTRIAL APPLICABILITY

The pest controlling composition of the present invention has an excellent pest controlling effect, thus, this composition is useful for controlling a pest.

The invention claimed is:

1. A pest controlling composition comprising spinetoram and a cyclic keto-enol compound having an acetyl CoA carboxylase-inhibiting activity as active ingredients, wherein the cyclic keto-enol compound having an acetyl CoA carboxylase-inhibiting activity is spirotetramat or spiromesifen, wherein the weight ratio of spinetoram to the cyclic keto-enol compound having an acetyl CoA carboxylase-inhibiting activity is from 20:1 to 1:200.

2. A method of controlling a pest, said method comprising applying an effective amount of spinetoram and an effective amount of a cyclic keto-enol compound having an acetyl CoA carboxylase-inhibiting activity to the pest or a habitat of the pest, wherein the cyclic keto-enol compound having an acetyl CoA carboxylase-inhibiting activity is spirotetramat or spiromesifen, wherein the weight ratio of spinetoram to the cyclic keto-enol compound having an acetyl CoA carboxylase-inhibiting activity is from 20:1 to 1:200.

* * * * *